United States Patent
Koch et al.

(10) Patent No.: US 9,670,133 B2
(45) Date of Patent: Jun. 6, 2017

(54) MIXTURES OF CANNABINOID COMPOUNDS, AND PRODUCTION AND USE THEREOF

(71) Applicant: SYMRISE AG, Holzminden (DE)

(72) Inventors: Oskar Koch, Göttingen (DE); Marcus Rudolf Götz, Oberweser (DE); Jan Looft, Wachtenberg-Niederbachem (DE); Tobias Vössing, Beverungen (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 14/653,044

(22) PCT Filed: Jun. 30, 2014

(86) PCT No.: PCT/EP2014/063872
§ 371 (c)(1),
(2) Date: Jun. 17, 2015

(87) PCT Pub. No.: WO2015/032519
PCT Pub. Date: Mar. 12, 2015

(65) Prior Publication Data
US 2015/0336874 A1    Nov. 26, 2015

(30) Foreign Application Priority Data

Sep. 3, 2013  (EP) .................................... 13182788

(51) Int. Cl.
| C07C 69/94 | (2006.01) |
| A61K 31/05 | (2006.01) |
| C07C 67/29 | (2006.01) |
| C07C 37/50 | (2006.01) |
| A61K 31/235 | (2006.01) |
| A61K 31/352 | (2006.01) |

(52) U.S. Cl.
CPC .............. C07C 69/94 (2013.01); A61K 31/05 (2013.01); A61K 31/235 (2013.01); A61K 31/352 (2013.01); C07C 37/50 (2013.01); C07C 67/29 (2013.01); C07C 2101/16 (2013.01)

(58) Field of Classification Search
None
See application file for complete search history.

(56) References Cited

FOREIGN PATENT DOCUMENTS

DE    10 2009 019322 A1    11/2010

OTHER PUBLICATIONS

A. F. Artamonov et al: "Synthesis of [alpha]-monoglycerides of aromatic acids", Chemistry of Natural Compounds, vol. 35, No. 4, Jul. 1, 1999, pp. 404-408, XP055090710.
Bela Szabo: "Pharmacology of Cannabinoid Receptors", Internet Citation, Jan. 1, 2008, pp. 1-13, XP002638928, Found in Internet: URL:http://www.slideshare.net/qnbs7/pharma.
International Search Report and Written Opinion under Rule 43 PCT attached to the Search Report, International Application No. PC/EP2014/063872.

*Primary Examiner* — Heidi Reese
(74) *Attorney, Agent, or Firm* — Polsinelli PC

(57) ABSTRACT

Specific compositions comprising one or multiple (cannabinoid) compound(s) of formula (A) and/or one or multiple salt(s) thereof are described as well as methods for their manufacture.

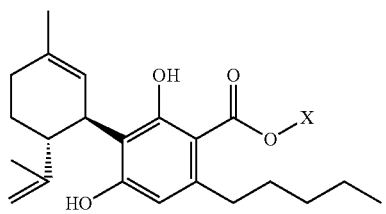

(A)

A compound of formula (A), a salt of formula (A) and a respective composition for use as medicine and for use in a method for the therapeutic treatment of the human or animal body, respectively, are also described.
Furthermore, corresponding pharmaceutical formulations, cosmetic preparations and foodstuff and/or gourmet or snack preparations fit for consumption as well as a method for the manufacture of delta-9-tetrahydrocannabinol are described.

10 Claims, 1 Drawing Sheet

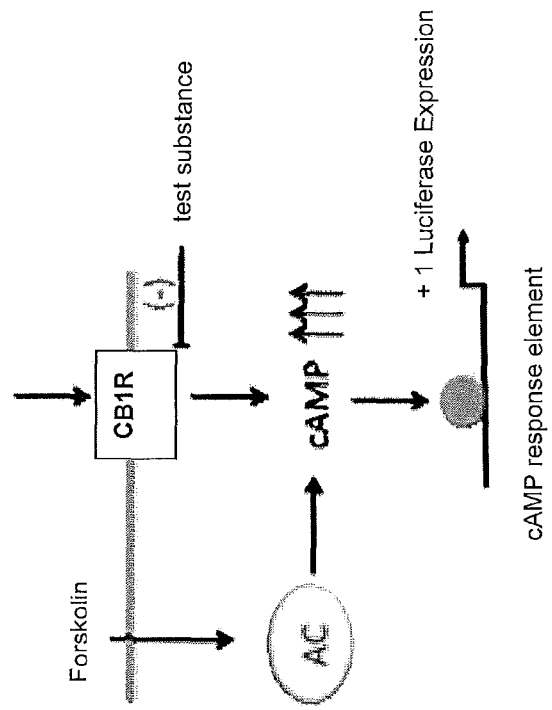
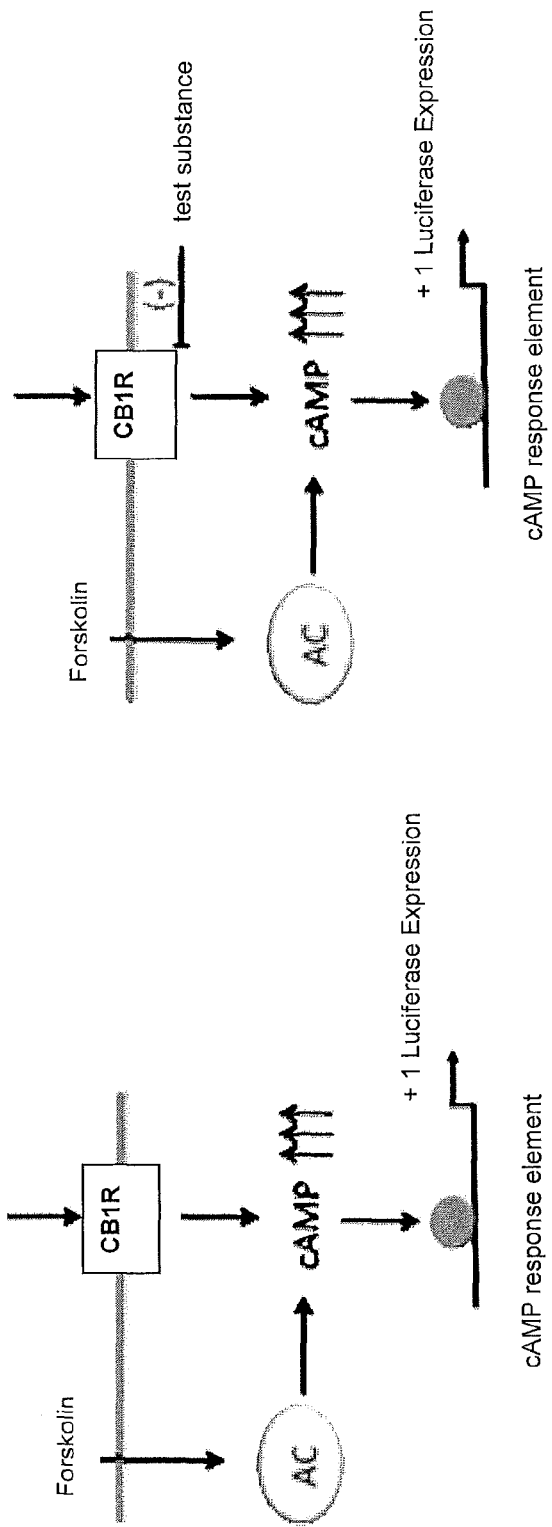

MIXTURES OF CANNABINOID COMPOUNDS, AND PRODUCTION AND USE THEREOF

CROSS REFERENCE TO RELATED APPLICATIONS

This application is a national stage application (under 35 U.S.C. §371) of PCT/EP2014/063872, filed Jun. 30, 2014, which claims benefit of European Application No. 13182788.3, filed Sep. 3, 2013, the entire contents of which is fully incorporated herein by reference.

The present invention relates to specific compositions comprising one or multiple (cannabinoid) compound(s) of formula (A) and/or one or multiple salts thereof

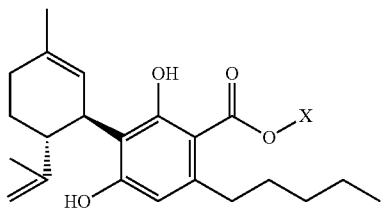

(A)

as well as methods for their manufacture. Please see below regarding the denotation of substituent X.

The invention also relates to a compound of the above formula (A), a salt of formula (A) and a composition comprising one or multiple (cannabinoid) compound(s) of formula (A) and/or one or multiple salt(s) thereof for use as a medicine and for use in processes for therapeutic treatment of the human or animal body, respectively.

Furthermore, the present invention relates to a compound of formula (A) and a salt of formula (A) and a composition comprising one of multiple cannabinoid compound(s) of formula (A), respectively, and/or one or multiple salt(s) thereof for specific use in methods for therapeutic treatment of the human or animal body for achieving an effect selected from the group consisting of appetite-stimulating effect, anti-emetic effect to inhibit nausea and vomiting, reduction of muscular cramps and spasticity, alleviation of pain symptoms, alleviation of migraine symptoms, reduction of intraocular pressure related to glaucoma, mood enhancement, immunostimulation and/or antiepileptic effect.

Moreover, the present invention relates to a pharmaceutical formulation comprising one or multiple compound(s) of formula (A) or comprising one or multiple salt(s) thereof or comprising a composition comprising one or multiple (cannabinoid) compound(s) of formula (A) and/or one or multiple salt(s) thereof, selected from the group consisting of solid galenic forms, dragées, capsules, granulates, powders, suppositories, lozenges, chewing gums, semi-solid forms, inhalants, injectables, implants and patches containing active ingredients.

Furthermore, the present invention relates to cosmetic preparations and foodstuff and/or gourmet or snack preparations fit for consumption comprising one or multiple compound(s) of formula (A) and/or salts thereof (as described herein).

The present invention also relates to a method for the manufacture of delta-9-tetrahydrocannabinol (delta-9-THC).

Furthermore, the present invention relates to particular compounds of formula (A) that are new with regard to the prior art and salts thereof.

Further aspects of the present invention arise from the following description as well as the enclosed patent claims.

Since the discovery of the endogenous cannabinoid system with its functional significance in terms of the regulation and modulation of the immune as well as the nervous system, there is an ongoing need for natural and artificial cannabinoids for their selective, pharmaceutical control. In particular, because of their different medical functions, there is a need for targeted, separate stimulation of the cannabinoid receptors CB1, which are mainly found in neurons, in highest density in basal ganglia, in the hippocampus and the cerebellum, and of the cannabinoid receptors CB2, which are mainly found on cells of the immune system and on cells that are involved in bone formation and bone loss.

The cannabinoid receptors CB1 and CB2 are presumed to be the accepted sites of action of molecules with a cannabinoid structure. Even though further receptors are discussed as potential CB3 receptors, it is assumed that the main effects are mediated via CB1 and CB2. Delta-9-THC, endogenous cannabinoids and a multitude of synthetic cannabinoids connect to said receptors and exert through them an effect on the cells (Pertwee, R. G. et al. *Pharmacol. Rev.* 2010, 62, 588-631).

CB1 and CB2 are members of the superfamily of the G protein coupled receptors (GPCRs). More precisely, the receptors inhibit the adenylate cyclase via the heteromeric G protein and activate the mitogenically activated protein kinase (Howlett, A. C. et al. *Pharmacol. Rev.* 2002, 54, 161-202; Howlett, A. C. *Handb. Exp. Pharmacol.* 2005, 168, 53-79). In terms of the CB1 receptor it is further described that it can modulate potassium flows via ion channels of the A-type and calcium flows via N as well as P/Q-type channels. Furthermore, CB1 receptors are able to transfer signals to the expressing cells via $G_s$ proteins (Glass, M., Felder, C. C. *J. Neurosci.* 1997; 17, 5327-5333; Maneuf, Y. P., Brotchie, J. M. *J. Pharmacol.* 1997; 120, 1397-1398; Calandra, B. et al. *Eur. J. Pharmacol.* 1999; 374, 445-455; Jarrahian, A. et al. *J. Pharmacol. Exp. Ther.* 2004, 308, 880-886).

The ability of CB1 and CB2 to transfer signals via $G_{i/o}$ and further downstream via inhibition of the adenylate cyclase, is used in the so-called [$^{35}$S]GTP gammaS binding assay and the cAMP assay (Howlett, A. C. et al. *Pharmacol. Rev.* 2002, 54, 161-202; Pertwee, R. G. *Handb. Exp. Pharmacol.* 2005a, 168, 1-51) to analyze the binding and signal transduction of cannabinoids.

CB1 receptors have at their disposal an orthosteric as well as one or multiple allosteric binding site(s), which are considered as potential sites of action for ligands (Price, M. R. et al. *Mol. Pharmacol.* 2005a, 68, 1484-1495; Adam, L. et al. 17*th Annual Symposium of the Cannabinoids,* 2007, S. 86; Horswill, J. G. et al. *J. Pharmacol.* 2007, 152, 805-814; Navarro, H. A. et al. *J. Pharmacol.* 2009, 156, 1178-1184). CB1 receptors are mainly found on the terminal ends of central and peripheral neurons, where they usually impart an inhibition of excitatory and inhibitory neurotransmitters (Howlett, A. C. et al. *Pharmacol. Rev.* 2002, 54, 161-202; Pertwee, R. G., Ross, R. A. *Prostaglandins Leukot Essent Fatty Acids,* 2002, 66, 101-121; Szabo, B., Schlicker, E. *Handb. Exp. Pharmacol.* 2005, 168, 327-365). The distribution of these receptors in the central nervous system is in such a way that their activation can influence different cognitive processes (e.g. alertness and memory, different motor functions and pain perception).

CB2 receptors are mainly localized, as mentioned before, in immune cells. Once they get activated, they modulate cell migration and the release of cytokines inside and outside the brain (Howlett, A. C. et al. *Pharmacol. Rev.* 2002, 54, 161-202; Cabral, G. A., Staab, A. *Handb. Exp. Pharmacol.* 2005, 168, 385-423; Pertwee, R. G. *Handb. Exp. Pharmacol.* 2005a, 168, 1-51).

There is also some evidence that firstly CB1 receptors are expressed by non-neuronal cells (including immune cells) (Howlett, A. C. et al. *Pharmacol. Rev.* 2002, 54, 161-202) and that secondly CB2 receptors are expressed by some cells inside and outside the brain (Skaper, S. D. et al. *Proc. Natl. Acad. Sci. USA* 1996, 93, 3984-3989; Ross, R. A. et al. *Neuropharmacology* 2001a, 40, 221-232; Van Sickle, M. D. et al. *Science* 2005, 310, 329-332; Wotherspoon, G. et al. *Neuroscience* 2005, 135, 235-245; Beltramo, M. et al. *Eur. J. Neurosci.* 2006, 23, 1530-1538; Gong, J. P. et al. *Brain Res.* 2006, 1071, 10-23; Baek, J. H. et al. *Acta Otolaryngol* 2008, 128, 961-967).

Known compounds, which have been proven to have an affinity for the aforementioned receptors CB1 and CB2, are amongst others cannabidiol (CBD) derived from representatives of the female hemp *Cannabis sativa* and *Cannabis indica* as well as certain chemical derivatives such as delta-8- and delta-9-tetrahydrocannabinol (delta-9-THC) or their oxidation product cannabinol (CBN).

*Cannabis* belongs to the family of Cannabidaceae. The botanical and chemotaxonomic classification of the genus *Cannabis* takes place according to two different procedural methods. Schultes et al. differentiates three types: *Cannabis sativa* Linnaeus, *Cannabis indica* LAM. and *Cannabis ruderalis* (Schultes, R. E. et al. *Harvard University Botanical Museum Leaflets* 1974, 23, 337-367). Others only name the one collective species *Cannabis sativa* L. from the subspecies *Cannabis sativa* ssp. *sativa* and ssp. *indica*.

According to the expert legal point of view, it is differentiated between a drug and a fiber type, whereby the differentiation occurs on the basis of the quantitative relationship of the main cannabinoids CBD and delta-9-THC.

Different cannabinoid compounds and methods for their manufacture are known from the prior art. WO 2006/136273 describes a method for the manufacture of dronabinol ((denoted (6aR-trans)-6a,7,8,10a-tetrahydro-6,6,9-trimethyl-3-pentyl-6H-dibenzo[b,d]pyran-1-ol, $\Delta^9$-tetrahydrocannabinol ($\Delta^9$-THC) in the WO document), nowadays according to IUPAC also denoted (6aR,10aR)-6,6,9-trimethyl-3-pentyl-6a,7,8,10a-tetrahydro-6H-benzo[c]chromen-1-ol or delta-9-tetrahydrocannabinol, delta-9-THC or Δ-9-THC) from cannabidiol (CBD) via cyclization of cannabidiol (CBD) (2-[1R-3-methyl-6-(1-methylethenyl)-2-cyclohexene-1-yl]-5-pentyl-1,3-benzenediol) to yield delta-9-THC. The described method is characterized in that cannabidiol (CBD) is provided in an organic solvent and is heated and cyclized to delta-9-THC in the presence of a molecular sieve. It is stated in WO 2006/136273 that the used molecular sieve exhibits, besides the drying properties that have been described so far, strong catalytic properties, which are in the focus of the described conversion. Cyclizations that can only be performed in the presence of a Lewis acid catalyst are usually significantly slower and deliver worse yields of delta-9-THC than cyclizations that are performed in the presence of a molecular sieve.

Further types of syntheses are described in the literature, e.g. by Crombie et al. *Chem. Research* 1977, 114, 1301-1345. More recent synthesis methods are disclosed inter alia in EP 2314580. The method for the manufacture of cannabinoids described therein, is supposed to be applicable to all stereoisomers and homologs of cannabinoids and consists of two and three chemical synthesis steps, respectively. In a first step, alkyl resorcylic acid esters (6-alkyl-2,4-dihydroxybenzoic acid ester) are thereby condensed with unsaturated hydrocarbons, alcohols, ketones (and their derivatives such as enol esters, enol ethers and ketals, respectively) to the corresponding 6-alkyl-2,4-dihydroxybenzoic acid esters that are substituted at the 3-position. In a second step, the ester function-containing intermediates that were produced in the first step are subjected to a decarboxylating saponification, giving rise to the corresponding ester-free cannabinoids. If necessary, an acid catalyzed rearrangement is carried out in a third step. This isomerization may be e.g. the ring closure of the pyran ring of CBD to give dronabinol, but also the rearrangement of a double bond like e.g. the reorganization of delta-9 to delta-8-THC or an acid catalyzed epimerization like the rearrangement of cis-9-ketocannabinoids to the corresponding trans-compounds.

U.S. Pat. No. 5,342,971 describes a method for the manufacture of dronabinol and of the related dibenzo[b,d] pyrans. These are produced, according to the abstract, through heating of a dihydroxybenzoic acid derivative in the presence of a Lewis acid catalyst and an inert non-polar solvent, in which indeed the dihydroxybenzoic acid is soluble, but the Lewis acid catalyst is insoluble or only very slightly soluble.

A typical embodiment comprises the production of intermediates that are useful for the synthesis of dronabinol and the related dibenzo[b,d]pyrans.

Delta-9-THC is, for example, approved as effective substance in the drug Marinol® in the United States since 1985 against anorexia, which occurs in patients under AIDS therapy, as well as against nausea and emesis, which occurs in connection with chemotherapy in cancer patients (tumor cachexia).

In Germany, delta-9-THC is listed in annex III of the Controlled Substances Act (CSA) and can be prescribed without restrictions of indications on a narcotic prescription. Since, however, no finished medicinal product is available on the market, either dronabinol in the form of Marinol® can exceptionally be prescribed and therefore can be imported from abroad, or a prescription preparation in a pharmacy according to accepted pharmaceutical rules can be carried out.

Furthermore, since May 2011 an extract of *Cannabis sativa* is approved as finished medicinal product under the name Sativex®. The approval applies to the additional treatment for improvement of symptoms in patients with moderately severe to severe spasticity due to multiple sclerosis that did not respond appropriately to another antispastic drug therapy. The drug contains an active agent combination of delta-9-THC and cannabidiol and is prescribed on a narcotic prescription. It is used as a spray in the oral cavity.

Provision No. 1164/89 of the European Commission denominates hemp with a (delta-9-THC) content of up to 0.3% relative to the dry matter as hemp for industrial purposes, whereas so-called drug hemp can have a content of 5%-15%.

Besides the extractive isolation from hemp, the partial synthesis from cannabidiol is possible. This precursor can be isolated from hemp grown for fiber and can then be acid-catalytically cyclized to delta-9-tetrahydrocannabinol as is described e.g. in WO 2006/136273.

One purpose of the present invention was to specify cannabinoid-active substances or compositions of substances (and methods for their manufacture) that exhibit a strong CB1 and CB2 affinity, respectively, in which preferably one of the two receptor affinities outweighs the other. The method to be provided was supposed to feature preferably a good space-time yield in connection with ecological advantages (preferable use of non-chlorinated solvents).

The substances or compositions of substances to be provided are supposed to be preferably used as medicines or in a method for therapeutic treatment of the human or animal body for achieving an effect selected from the group consisting of appetite-stimulating effect, anti-emetic effect to inhibit nausea and vomiting, reduction of muscular cramps and spasticity, alleviation of pain symptoms, alleviation of migraine symptoms, reduction of intraocular pressure related to glaucoma, mood enhancement, immunostimulation and/or antiepileptic effect.

The present invention is based inter alia on the surprising realization that compounds of formula (A) as well as salts thereof, wherein substituent X in formula (A) is an aliphatic residue without or with one, two, three or more than three hydroxyl group(s), wherein the total number of C-atoms in the aliphatic residue X is not greater than 15, preferably not greater than 12, and
wherein the aliphatic residue
  is saturated or unsaturated,
and
  is branched or unbranched,
and
  is acyclic or cyclic,
exhibit an advantageous and unique binding affinity for the cannabinoid receptors CB1 and CB2, whereby they lend themselves to the use as medicines or to the use in a method for therapeutic treatment of the human or animal body.

The use of one or multiple compound(s) of formula (A) (as defined above and in the following, especially in the claims) or of one or multiple salt(s) thereof or of a corresponding composition (as defined above and in the following, especially in the claims) as medicine and in a method for therapeutic treatment of the human or animal body, respectively, specifically aims at achieving an effect selected from the group consisting of
  appetite-stimulating effect,
  anti-emetic effect to inhibit nausea and vomiting,
  reduction of muscular cramps and spasticity,
  alleviation of pain symptoms,
  alleviation of migraine symptoms,
  reduction of intraocular pressure related to glaucoma,
  mood enhancement,
  immunostimulation
and/or
  antiepileptic effect.

In own tests particularly the following substances III-V and XI-XIII with the generic formula (A) were analyzed regarding their effect on cannabinoid receptors.

III

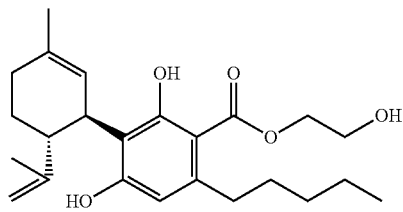

IV

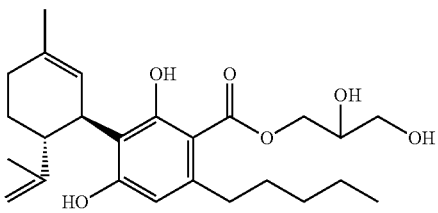

V

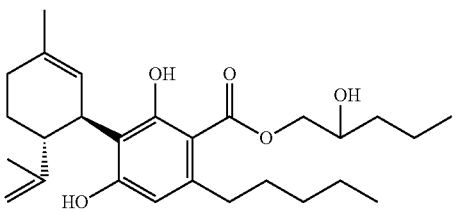

XI

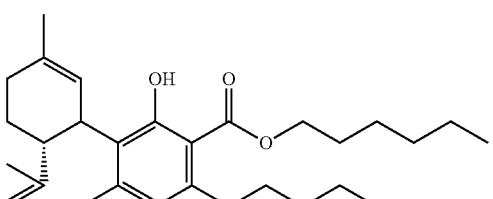

XII

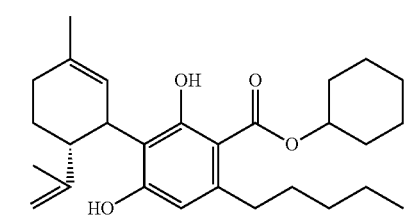

XIII

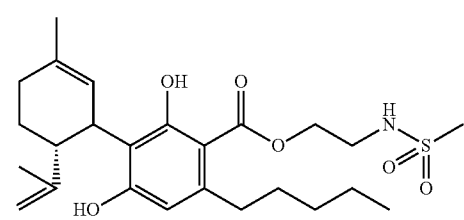

Substances III-V and XI-XIII were—representatively for the compounds of formula (A) described herein—analyzed in competition studies regarding their binding affinity and their resulting binding profile for CB1 and CB2 receptors. For details, it is particularly referred to the examples below. The studies have revealed in particular that the cannabinoid substances III-V and XI-XIII bind to cannabinoid receptors in nanomolar concentrations and therefore in physiological doses. They are weak ligands for CB1 receptors and bind preferentially to CB2 receptors. Their selectivity for CB2 receptors predestines them for use as CB2 receptor modulators.

Therefore, the use of one or multiple compound(s) of formula (A) (as defined above and in the following, especially in the claims) or of one or multiple salt(s) thereof or of a corresponding composition (as defined above and in the following, especially in the claims) is particularly preferred, particularly of one or multiple compound(s) selected from the group consisting of the compounds III-V and XI-XIII, of one or multiple salt(s) thereof or of corresponding compositions, as CB1 and/or CB2 receptor modulators.

The modulators described herein can have agonistic or antagonistic effects (please refer to the examples for comparison).

Compounds III, IV, V, XI and XIII as described herein as well as the salts thereof or corresponding compositions are, for example, particularly preferable CB2 agonists.

Compounds IV and XI as well as the salts thereof or corresponding compositions are, for example, preferable CB1 agonists. Compounds III, V, XII and XIII as well as the salts thereof or corresponding compositions are, for example, preferable CB1 antagonists.

Compounds of formula (A) (as defined above and in the following, especially in the claims) therefore solve the problem described above because of their specific CB1 and CB2 receptor affinity, respectively, please compare again to the examples further below.

Thus, the invention relates to a compound of formula (A) (as defined above and in the following, especially in the claims) or a salt of a compound of formula (A) (as defined above and in the following, especially in the claims) or a composition (as defined above and in the following, especially in the claims)
(i) for use as medicine
or
(ii) for use in a method for the therapeutic treatment of the human or animal body.

Preferred is such a compound of formula (A) (as defined above and in the following, especially in the claims) or such a salt of a compound of formula (A) (as defined above and in the following, especially in the claims) or such a composition (as defined above and in the following, especially in the claims) for the specific use in a method for the therapeutic treatment of the human or animal body to achieve an effect selected from the group consisting of
- appetite-stimulating effect,
- anti-emetic effect to inhibit nausea and vomiting,
- reduction of muscular cramps and spasticity,
- alleviation of pain symptoms,
- alleviation of migraine symptoms,
- reduction of intraocular pressure related to glaucoma,
- mood enhancement,
- immunostimulation and/or
- antiepileptic effect.

Moreover, the invention relates to a pharmaceutical formulation comprising one or multiple compound(s) of formula (A) (as defined above and in the following, especially in the claims) or comprising one or multiple salt(s) thereof (as defined above and in the following, especially in the claims) or comprising a corresponding composition (as defined above and in the following, especially in the claims). The pharmaceutical formulation according to this invention is preferably selected from the group consisting of
- solid galenic forms,
- dragées,
- capsules,
- granulates,
- powders,
- suppositories,
- lozenges,
- chewing gums,
- semi-solid forms,
- inhalants,
- injectables,
- implants and
- patches containing active ingredients.

Alternatively, the pharmaceutical formulation is available in liquid form.

Preferred pharmaceutical formulations are:

Solid galenic forms (e.g. tablets (with coating or without, with modified release or without), dragées (with coating or without, with modified release or without), capsules (soft or hard gelatin capsules with modified release or without), granulates (with modified release or without), powders (with modified release or without, e.g. nose powders, ear powders), suppositories (with coating or without, with modified release or without), lozenges, chewing gums, semi-solid forms (e.g. hydrophobic ointments amongst them e.g. hydrocarbon gels, lipogels, silicon gels, oleo gels as well as water-absorbing ointments amongst them e.g. absorption bases, hydrophilic ointments, hydrophilic gels (hydrogels) or pastes, also nasal ointments), inhalants (e.g. pressure gas metered dose inhalers, powder inhalers, inhalers with nebulizers, inhalation concentrates for inhalation), injectables and implants (e.g. on the basis of liquid or solid forms that are suitable for the preparation of or use as injectable solutions or solid matrices that enable modified release), patches containing active ingredients, ear tampons.

Liquid forms are e.g. solutions, suspensions, emulsions, syrups (colloquially cough syrup), mouthwashes, gargle solutions, throat sprays or nasal sprays, nose drops, nasal rinsing solutions, ear drops, ear sprays and ear rinsing solutions.

Pharmaceutical formulations comprising one or multiple compound(s) of formula (A) (as defined above and in the following, especially in the claims) and/or one or multiple salt(s) thereof (as defined above and in the following, especially in the claims) and/or corresponding compositions (as defined above and in the following, especially in the claims) for use as a medicine or for use in a method for the therapeutic treatment of the human or animal body preferably contain one or multiple component(s) selected from the following group: Filling material (e.g. cellulose, calcium carbonate), flow agents and anti-caking agents (e.g. talcum, magnesium stearate), coatings (e.g. polyvinyl acetate phthalate, hydroxypropyl methylcellulose phthalate), disintegrants (e.g. starch, crosslinked polyvinylpyrrolidone), plasticizers (e.g. triethyl citrate, dibutyl phthalate), substances for granulation (lactose, gelatin), retardation (e.g. poly (meth)acrylic acid-methyl/ethyl/2-trimethyl-aminoethyl ester copolymers in dispersion, vinyl acetate/crotonic acid copolymers), compacting (e.g. microcrystalline cellulose, lactose), solvents, suspension or dispersing agents (e.g. water, ethanol), emulsifying agents (e.g. cetyl alcohol, lecithin), substances for modification of rheological properties (silicon dioxide, sodium alginate), substances for microbial stabilization (e.g. benzalkonium chloride, potassium sorbate), preservatives and antioxidants (e.g. DL-alpha-tocopherol, ascorbic acid), substances for modification of the pH value (lactic acid, citric acid), propellant or inert gas (e.g. fluorinated chlorinated hydrocarbons, carbon dioxide), colorants (iron oxide, titanium oxide), ointment base materials (e.g. paraffin wax, beeswax), inter alia as they can be found in the technical literature (e.g. Schmidt, P. C., Christin, I. "*Wirk- und Hilfsstoffe für Rezeptur, Defektur und Großherstellung*", 1999, Wissenschaftliche Verlagsgesellschaft mbH Stuttgart or Bauer, K. H., Frömming, K-H., Führer, C. "*Lehrbuch der Pharmazeutischen Technologie*", 8. Auflage, 2006, Wissenschaftliche Verlagsgesellschaft mbH Stuttgart).

The preferably used amounts of one or multiple compound(s) of formula (A) (as defined above and in the following, especially in the claims) and/or one or multiple salt(s) thereof (as defined above and in the following, especially in the claims) and/or corresponding compositions (as defined above and in the following, especially in the claims) as well as of the above mentioned components in a pharmaceutical formulation, can easily be determined by a person skilled in the art by simple trial and error methods dependent on the kind and purpose of the respective formulation.

The compounds of formula (A) and salts thereof described herein are advantageously also suitable for use in cosmetic preparations. Furthermore, they are suitable for use in gourmet or snack preparations and/or foodstuffs fit for consumption. The preferably used amounts of one or multiple compound(s) of formula (A) (as defined above and in the following, especially in the claims) and/or of one or multiple salt(s) thereof (as defined above and in the following, especially in the claims) and/or of the corresponding compositions (as defined above and in the following, especially in the claims) in such preparations can easily be determined by a person skilled in the art by simple trial and error methods dependent on the kind and purpose of the respective formulation. Concerning the remaining components of the preparation, they are otherwise usual components for such preparations.

The amount of compound(s) of formula (A) and/or salts thereof contained in a formulation and preparation, respectively, according to the present invention is preferably sufficient to achieve one or multiple effect(s) selected from the group consisting of
- appetite-stimulating effect,
- anti-emetic effect to inhibit nausea and vomiting,
- reduction of muscular cramps and spasticity,
- alleviation of pain symptoms,
- alleviation of migraine symptoms,
- reduction of intraocular pressure related to glaucoma,
- mood enhancement,
- immunostimulation
and
- antiepileptic effect.

when used and during use or consumption, respectively.

The present invention also relates to a composition comprising one or multiple compound(s) of formula (A) and/or one or multiple salt(s) thereof, preferably one or multiple pharmaceutically acceptable salt(s) of a compound of formula (A)

(A)

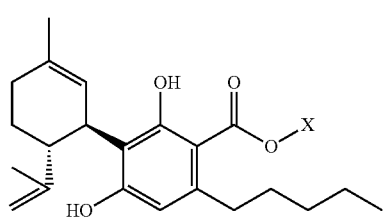

wherein X is an aliphatic residue without or with one, two, three or more than three hydroxyl groups, wherein the total number of C-atoms in the aliphatic residue X is not greater than 15, preferably not greater than 12,
and wherein the aliphatic residue
  is saturated or unsaturated,
and
  is branched or unbranched,
and
  is acyclic or cyclic, wherein the molar ratio of the total amount of compounds of formula (A) and salts thereof, preferably pharmaceutically acceptable salts, in the composition to the amount of cannabidiol (if present) is greater than 1:1, preferably greater than 5:1, most preferably greater than 10:1
and simultaneously
the molar ratio of the total amount of compounds of formula (A) and salts thereof, preferably pharmaceutically acceptable salts, to the amount of compounds of formula (I) (if present)

(I)

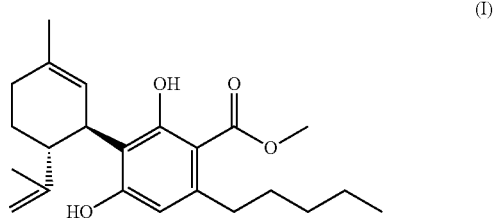 [SMILES: C=C(C)[C@@H]1CCC(C)=C[C@H]1c1c(O)cc(CCCCC)c(C(=O)OC)c1O]

is greater than 1:1, preferably greater than 5:1, most preferably greater than 10:1.

In case the aliphatic residue X of a compound of formula (A) has one or multiple chiral center(s), each of the possible configurations at the or each of these chiral center(s), respectively, are equal (R or S). In case not specified otherwise in a specific case, a graphically presented, individual compound of formula (A) in the present text with one or multiple chiral center(s) at the aliphatic residue denominates all of the configuration isomers and likewise all of the compositions of configuration isomers of the depicted compound, in case they are representable via the adjustment of the configuration at the chiral center(s) of the aliphatic residue.

Depending on the desired design and purpose, compositions according to the invention (as defined above and in the following, especially in the claims) can contain one or multiple component(s) as described above in relation to pharmaceutical formulations according to the invention. Compositions according to the present invention can also be semi-finished products for the manufacture of further compounds of the cannabinoid group, which in turn are used themselves for the manufacture of pharmaceutical formulations.

Cannabidiol can be manufactured from a compound of formula (A) via decarboxylation and saponification analogous to EP 2 314 580 A1. In a composition according to the invention the total amount of compounds of formula (A) and salts thereof outweigh the amount of cannabidiol (if present).

The compound(s) of formula (A) can be produced via transesterification of cannabidiolic acid methyl ester of the formula (I); however, in a composition according to the invention the total amount of compounds of formula (A) and salts thereof outweigh the amount of methyl ester of formula (I) (if present).

Hence, cannabidiol and/or cannabidiolic acid methyl ester (I) can be present in compositions according to the invention; however, their presence is not compulsory.

If a composition according to the invention comprises only one single compound of formula (A) and a single salt of this single compound of formula (A), respectively, it contains at least one further component. See above regarding preferred components.

Hence, a composition according to the invention comprises for instance (i) a single compound or (ii) a single salt or (iii) multiple compounds or (iv) multiple salts or (v) one compound and one salt or (vi) multiple compounds and one or multiple salt(s) or (vii) different salts of the same compound with the same deprotonation pattern (but with different cations) or (viii) salts of the same compound with the same cation that differ in their degree of deprotonation or (ix) salts of the same compound, but with the same or different cations that differ in their degree of deprotonation or (x) salts of different compounds with the same pattern of deprotonation and the same cations or (xi) salts of different compounds with different patterns of deprotonation and the same or different cations or (xii) salts of different compounds with different patterns of deprotonation and different cations.

Certain compounds of formula (A) (as defined above) may possibly be formed intermediately during the process described in EP 2314580, however, the compound and compounds of formula (A), respectively, would only be present in trace amounts or only in small quantities compared to the amount of compounds (I) and the amount of cannabidiol. However, herein described are also selected compounds of formula (A) that are not known from the prior art yet, e.g. compounds III, IV and V as well as XI, XII and XIII:

III

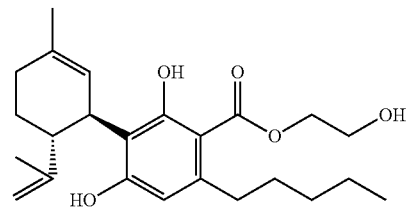

IV

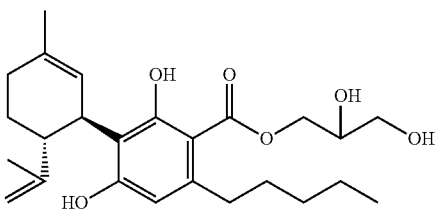

V

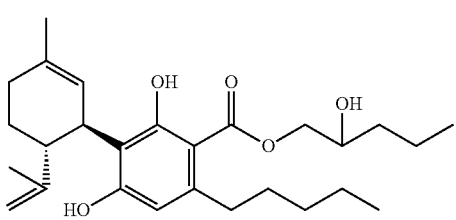

XI

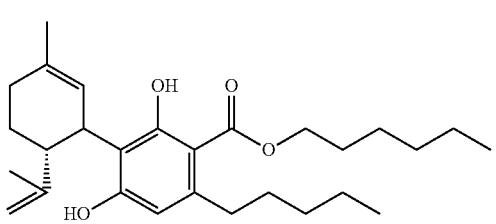

XII

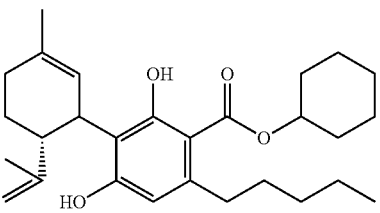

XIII

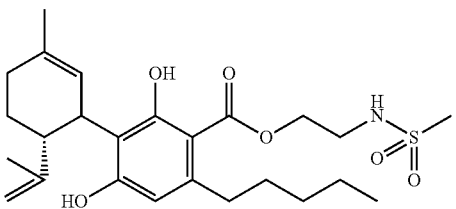

The same applies to their salts.

Preferably, a composition according to the invention is made up in such a way that the ratio of the total amount of compounds of formula (A) and salts thereof in the composition in relation to the total weight of the composition is 0.0001 to 100 wt.-%, more preferably 0.001 to 100 wt.-%, most preferably 0.1 to 100 wt.-%, more preferably 1 to 100 wt.-%. That is, compositions according to the invention, which not only comprise one single compound of formula (A) and a single salt of this single compound of formula (A), respectively, can be comprised in a way that they consist exclusively (100 wt.-%) of compounds of formula (A) and/or salts thereof.

For salts of compounds of formula (A) according to the invention the following applies: Where appropriate one or multiple hydroxyl group(s) of a compound of formula (A) exist in a deprotonated form. In addition to the (deprotonated) compound(s) of formula (A) a corresponding amount of counter cations is present, wherein these are preferably selected from the group consisting of: singly positively charged cations of the first main group and first group of transition elements, ammonium ions, trialkylammonium ions, doubly positively charged cations of the second main group and second group of transition elements as well as triply positively charged cations of the third main group and third group of transition elements, as well as compositions thereof.

The phenolic hydroxyl groups of a compound of formula (A) are regularly more acidic than hydroxyl groups in the aliphatic side chain (if present).

The corresponding amount of counter cations (depending on their charge) results from the number of deprotonated hydroxyl groups. It arises, for example, from a compound of formula (A) with two phenolic hydroxyl groups underlying such a salt, that, in case of full deprotonation of these phenolic hydroxyl groups, a doubly negatively charged anion exists, whereof the number of positive charges (in this case: two) can be derived that have to be provided by the counter cation(s). Most preferably these counter cations are cations selected from the group consisting of $Na^+$, $K^+$, $NH_4^+$, $Ca^{2+}$, $Mg^{2+}$, $Al^{3+}$ and $Zn^{2+}$.

Preferred is a composition according to the invention, wherein the molar ratio of the total amount of compounds of formula (A) and salts thereof to the total amount of compounds of formula (II)

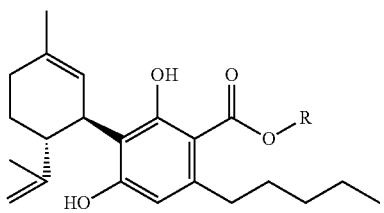

(II)

(that is, compounds of formula (I) and other compounds of formula (II))
is greater than 1:1, preferably greater than 5:1, most preferably greater than 10:1,
wherein R is selected from the group consisting of H and protecting groups.

The term protecting groups thereby comprises all groups that are to be regarded as protecting groups according to EP 2314580 A1. According to section [0040] of EP 2314580 A1, a carboxyl protecting function (definition analogous to Herlt U.S. Pat. No. 5,342,971, p. 4) with one to up to 16 carbon atoms, typically an alkyl function or a substituted alkyl function such as benzyl (phenylmethyl-), diphenylmethyl- or alkyl residues with one to 16 C-atoms that are substituted in the 2-position such as (i) lower alkoxy-, e.g. 2-methoxyethyl, 2-ethoxyethyl, (ii) lower alkylthio such as 2-methylthioethyl and 2-ethylthioethyl, (iii) halogen such as 2,2,2-trichloroethyl, 2-bromoethyl and 2-chloroehtyl, (iv) one or two phenyl groups (substituted or unsubstituted), substituted alkyl groups, as well as aroyl groups such as phenacyl are suitable for R. The aliphatic residues with one, two, three or more than three hydroxyl groups, wherein the total number of C-atoms in the aliphatic residue X is not greater than 15 that are contained in compounds of formula (A), are not considered to be protecting groups.

Thus, also in preferred compositions according to the invention cannabidiol (R=H) and/or cannabidiolic acid methyl ester (I) (R=Me) and/or further compounds of formula (II) as defined above can be present, however, their presence is neither compulsory nor shall their total amount be greater than the total amount of compounds of formula (A) and salts thereof. Compositions according to the invention, in which the molar ratio of the total amount of compounds of formula (A) and salts thereof to the total amount of compounds of formula (II) is greater than 5:1, most preferably greater than 10:1, have proven to be particularly advantageous regarding their properties (as described above and in the following) and/or their use in methods according to the invention, since that way competing reactions of the compounds of formula (II) as described above with compounds of formula (A) at CB1 and CB2 receptor sites, respectively, are repressed as well as significant yield losses in the subsequent conversions of compositions according to the invention in methods according to the invention are frequently avoided.

A composition according to the invention (as defined above and in the following, especially in the claims) is preferred according to one aspect of the present invention, in which the number of hydroxyl groups at the aliphatic residue X is one, two or three, preferably one or two. Compositions according to the invention in which compounds of the formula (A) and salts thereof, respectively, carry one, two or three, preferably one or two hydroxyl groups at the aliphatic residue X, haven proven to be particularly advantageous in own studies. These compounds possess in fact the solubility, which is required for the applications and reactions, respectively, as described above or in the following because of the presence of the said one, two or three, preferably one or two hydroxyl groups at the aliphatic residue, however, they don't possess such a large number of aliphatic hydroxyl groups that undesired side reactions such as elimination reactions occur to a bothersome extent.

Particularly in case the aliphatic residue X of a compound of formula (A) does not exhibit any hydroxyl groups (as described herein), the following preferably applies to residue X: it is an aliphatic residue, wherein the total number of C-atoms in the aliphatic residue is at least 2 and 8 at the most, preferably at least 3 and 6 at the most. Most preferably such a compound is selected from the compounds XI, XII and XIII as described herein. The same applies accordingly to salts of compounds of formula (A).

A composition according to the invention is preferred, wherein the aliphatic residue of the compound of formula (A) is saturated and/or unbranched, preferably saturated and unbranched.

Compositions according to the invention, wherein the aliphatic residue of the compound of formula (A) is saturated and/or unbranched, preferably saturated and unbranched, have proven to be specifically advantageous, since unsaturated aliphatic residues increase the risk of unwanted side reactions and branched aliphatic residues usually do not fulfill the steric requirements of compositions according to the invention to the same extent (particularly for the use as medicine or the use in a method for the therapeutic treatment of the human and animal body).

Below, preferred compounds of formula (A) and compositions containing such compounds, respectively, whose residues X exhibit one or multiple hydroxyl group(s), are described.

A composition according to the invention is preferred, wherein the compound of formula (A) is a compound of the formula (A-I)

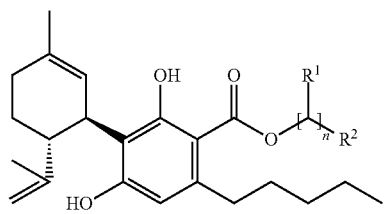

(A-I)

wherein the following applies:
each $R^1$ represents independently of the meaning of any other of the overall n $R^1$ residues H, alkyl with one or two C-atoms or OH
$R^2$ represents H or OH
n represents an integer in the range of 2 to 10,
wherein at least one of the residues $R^1$ or the residue $R^2$ represent OH.

Own studies revealed that the properties of such preferred compositions according to the invention are particularly advantageous, presumably because they contain compounds of the formula (A-I) whose longest aliphatic side chain consists of not more than 12 carbon atoms.

A composition according to the invention is preferred, wherein the compound of formula (A) is a compound of the formula (A-II)

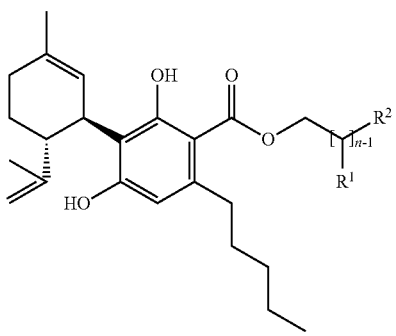

wherein the following applies:
each $R^1$ represents independently of the meaning of any other of the overall n-1 $R^1$ residues H, alkyl with one or two C-atoms or OH
$R^2$ represents H or OH
n represents an integer in the range of 2 to 10,
wherein at least one of the residues $R^1$ or the residue $R^2$ represent OH.

Furthermore, own studies revealed that compositions according to the invention that comprise compounds of the formula (A-II), exhibit particularly specific CB1 and CB2 receptor affinities. Thus, it is preferred that a divalent methylene group (—$CH_2$—) or (in case $R^1$=H) a divalent alkylene group is located in close proximity of the carboxyl group.

Particularly preferred is a composition according to the invention, wherein the compound of formula (A) is
(i) a compound of formula
(A-III)

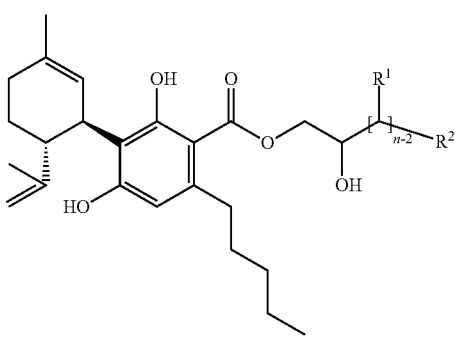

wherein the following applies:
each $R^1$ represents independently of the meaning of any other of the overall n-2 $R^1$ residues H, alkyl with one or two C-atoms or OH
$R^2$ represents H or OH
n represents an integer in the range of 2 to 10, preferably in the range of 3 to 10
wherein at least one of the residues $R^1$ or the residue $R^2$ represent OH
and/or
(ii) a compound of formula (A-IV)

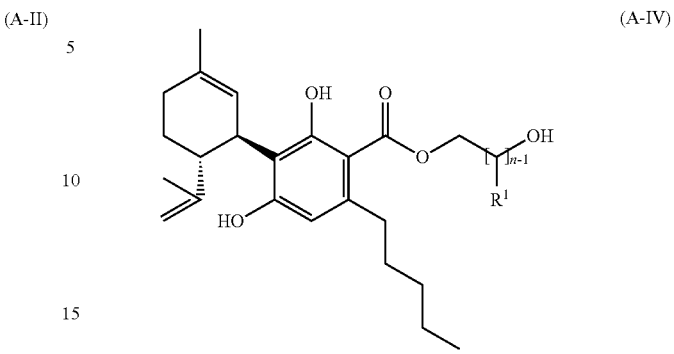

wherein the following applies:
each $R^1$ represents independently of the meaning of any other of the overall n-1 $R^1$ residues H, alkyl with one or two C-atoms or OH
n represents an integer in the range of 2 to 10.

Such compounds of formulas (A-III) and (A-IV) possess at least one hydroxyl group in the aliphatic side chain and a divalent methylene group (—$CH_2$—) and (in case $R^1$ of formula (A-IV) is H) an alkylene group, respectively, in close proximity of the carboxyl group. Own structure-activity measurements (cp. inter alia tables 1 and 2 of example "A. Studies on the effect of compounds according to the invention on cannabinoid receptors") showed that a hydroxyl group in a terminal position (in formula (A-IV)) as well as a hydroxyl group located at the carbon atom that is in the immediate proximity of the divalent methylene group (formula (A-III), have a particularly advantageous influence on the desired properties of the composition according to the invention.

Further preferred is a composition according to the invention (as defined above and in the following, especially in the claims), wherein in the said formulas (A-I), (A-II), (A-III) and (A-IV), respectively, each $R^1$ represents independently of the meaning of any other of the $R^1$ residues H or OH.

A composition according to the invention is also preferred, which comprises one or multiple salt(s) of the compounds of formulas (A-I), (A-II), (A-III) and (A-IV), respectively (as defined above and in the following, especially in the claims).

Particularly preferred is a composition according to the invention (as defined above and in the following, especially in the claims), wherein the compound of formula (A) is selected from the group consisting of:

III

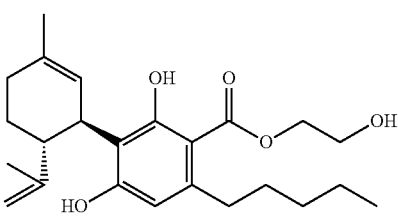

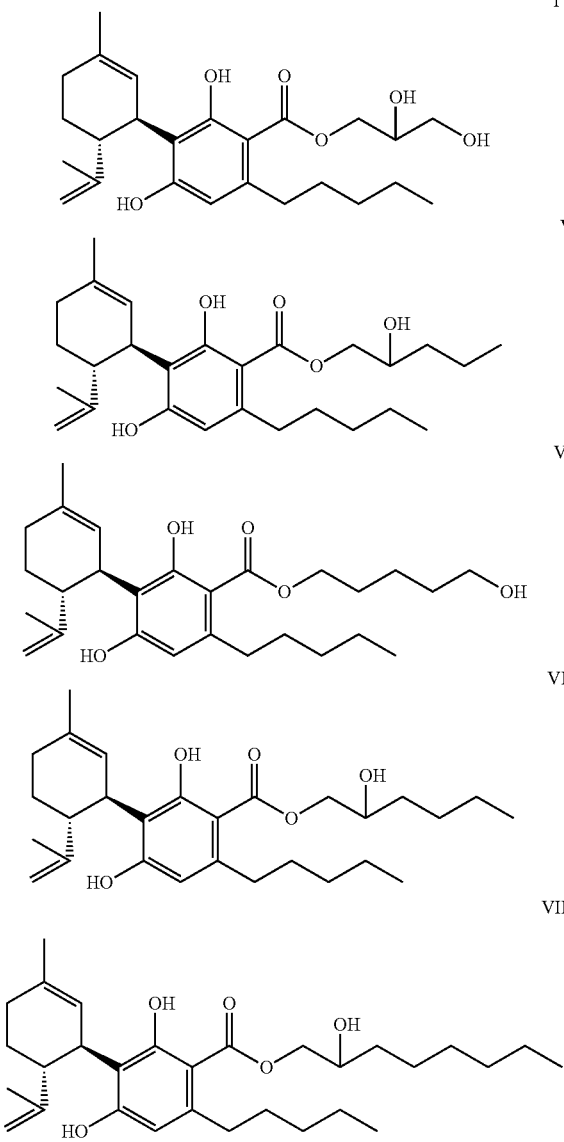

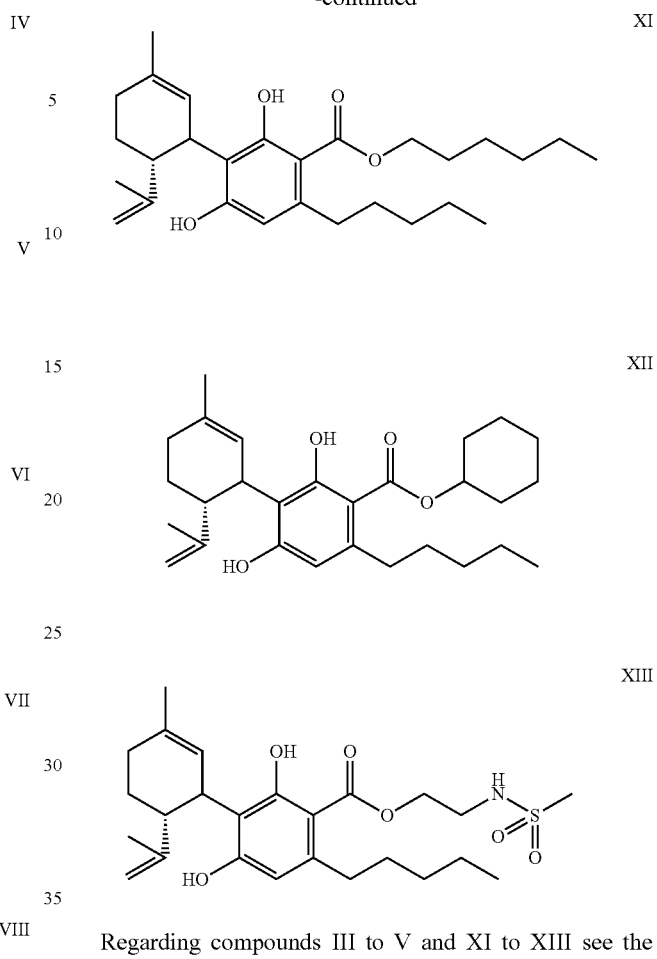

Regarding compounds III to V and XI to XIII see the specified properties and advantages above and in the examples; very similar properties and advantages also exist for compounds VI to VIII, the remarks concerning compounds III to V apply mutatis mutandis. As a matter of course, the salts of compounds III-VIII as well as XI-XIII (as defined above and in the following, especially in the claims) are also preferably used.

Compounds III-VIII are defined as follows by formulas A-I, A-II, A-III, A-IV.

| Formula | | Compound III | Compound IV | Compound V |
|---|---|---|---|---|
| (A) | X | $OCH_2CH_2OH$ | $OCH_2CH(OH)CH_2OH$ | $OCH_2CH(OH)CH_2CH_2CH_3$ |
| (A-I) | 1. $R^1$ | H | H | H |
| | 2. $R^1$ | H | OH | OH |
| | 3. $R^1$ | / | H | H |
| | 4. $R^1$ | / | / | H |
| | 5. $R^1$ | / | / | / |
| | 6. $R^1$ | / | / | / |
| | 7. $R^1$ | / | / | / |
| | $R^2$ | OH | OH | $CH_3$ |
| | n | 2 | 3 | 4 |
| (A-II) | 1. $R^1$ | H | OH | OH |
| | 2. $R^1$ | / | H | H |
| | 3. $R^1$ | / | / | H |
| | 4. $R^1$ | / | / | / |
| | 5. $R^1$ | / | / | / |
| | 6. $R^1$ | / | / | / |
| | $R^2$ | OH | OH | $CH_3$ |
| | n | 2 | 3 | 4 |
| (A-III) | 1. $R^1$ | / | H | H |
| | 2. $R^1$ | / | / | H |
| | 3. $R^1$ | / | / | / |

-continued

| | | Compound V | Compound V | Compound V |
|---|---|---|---|---|
| | 4. $R^1$ | / | / | / |
| | 5. $R^1$ | / | / | / |
| | $R^2$ | / | OH | $CH_3$ |
| | n | / | 3 | 4 |
| (A-IV) | 1. $R^1$ | H | OH | / |
| | 2. $R^1$ | / | H | / |
| | 3. $R^1$ | / | / | / |
| | 4. $R^1$ | / | / | / |
| | n | 2 | 3 | / |

| Formula | | Compound VI | Compound VI | Compound VIII |
|---|---|---|---|---|
| (A) | X | $O(CH_2)_5OH$ | $OCH_2CH(OH)CH_2(CH_2)_2CH_3$ | $OCH_2CH(OH)CH_2(CH_2)_4CH_3$ |
| (A-I) | 1. $R^1$ | H | H | H |
| | 2. $R^1$ | H | OH | OH |
| | 3. $R^1$ | H | H | H |
| | 4. $R^1$ | H | H | H |
| | 5. $R^1$ | H | H | H |
| | 6. $R^1$ | / | / | H |
| | 7. $R^1$ | / | / | H |
| | $R^2$ | OH | $CH_3$ | OH |
| | n | 5 | 5 | 7 |
| (A-II) | 1. $R^1$ | H | OH | OH |
| | 2. $R^1$ | H | H | H |
| | 3. $R^1$ | H | H | H |
| | 4. $R^1$ | H | H | H |
| | 5. $R^1$ | / | / | H |
| | 6. $R^1$ | / | / | H |
| | $R^2$ | OH | $CH_3$ | $CH_3$ |
| | n | 5 | 5 | 7 |
| (A-III) | 1. $R^1$ | / | H | H |
| | 2. $R^1$ | / | H | H |
| | 3. $R^1$ | / | H | H |
| | 4. $R^1$ | / | / | H |
| | 5. $R^1$ | / | / | H |
| | $R^2$ | / | $CH_3$ | $CH_3$ |
| | n | / | 5 | 7 |
| (A-IV) | 1. $R^1$ | H | / | / |
| | 2. $R^1$ | H | / | / |
| | 3. $R^1$ | H | / | / |
| | 4. $R^1$ | H | / | / |
| | n | 5 | / | / |

The invention also relates to a method for the manufacture of a composition according to the invention (as defined above and in the following, especially in the claims), including the following step:

Conversion of a cannabidiolic acid ester of formula (IX)

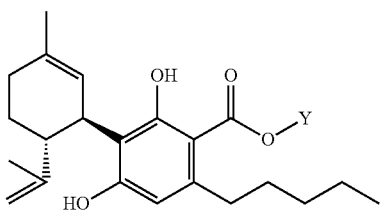

(IX)

wherein Y is an organic residue,
with an alcohol of the formula HO—X,
wherein
X is an aliphatic residue without or with one, two, three or more than three hydroxyl groups, wherein the total number of C-atoms in the aliphatic residue X is not greater than 15, preferably not greater than 12, and
wherein the aliphatic residue is
  saturated or unsaturated
and
  branched or unbranched
and
  acyclic or cyclic, wherein Y is different from X and selected in such a way that the alcohol of formula HO—Y, which is generated during the conversion, boils at a lower temperature at 1013 hPa than the used alcohol of formula HO—X.

The product of the method according to the invention is a composition according to the invention.

During the conversion of a cannabidiolic acid ester of formula (IX) with alkali in high-boiling solvents of the formula HO—X without the presence of water it was surprisingly found that this conversion did not lead directly to the cannabidiolic acid, but to the corresponding transesterification product, i.e. a compound of formula (A). This compound could be isolated from the reaction composition in high yield. Besides their capacity as CB1/CB2 receptor agonists or antagonists, these compounds of formula (A) can also be used for the synthesis of cannabidiol and delta-9-THC, respectively.

In contrast, EP 2314580 A1 describes the saponification of compound (I) to cannabidiol through treatment with alkali in a composition of methanol/water, wherein the reaction is carried out under pressure at 140-150° C. Alternatively, the reaction can be carried out "at zero pressure" using a "water-miscible solvent with a boiling point of over 100° C. at standard pressure". Compounds of formula (A) (as defined above) are not identified and not isolated according to EP 2314580 A1.

Previous methods for the manufacture of cannabidiol or cannabinoid compounds, which comprise the following steps:

a) Coupling of a suitable terpene with a resorcinol derivative (step I),
b) Saponification and decarboxylation of the ester group of the resorcinol derivative (step II) and
c) Cyclization of the intermediate to yield cannabidiol (step III)

include the following disadvantages using the specified procedural method, particularly regarding a technical production:

Cooling of the reaction through low temperatures (step I) and long reaction time, which negatively influences the economic efficiency of the process in terms of energy consumption on one hand and the relatively long working time on the other hand, Use of volatile methylene chloride (step I and III), which is classified as being noxious and potentially carcinogenic and which, through the required high safety measures during exposure, also negatively influences the economic efficiency and the ecological compatibility of the process High dilution and therefore poor space-time yield (step I and III).

Particularly preferred is a method of manufacture according to the invention of a composition according to the invention, wherein Y is an alkyl group, which is preferably selected from the group consisting of methyl, ethyl, n-propyl, iso-propyl, n-butyl, sec-butyl, iso-butyl, tert-butyl.

The alkyl groups methyl, ethyl, n-propyl, iso-propyl, n-butyl, sec-butyl, iso-butyl, tert-butyl turned out to be advantageous residues Y during the conversion of a cannabidiolic acid ester of formula (IX) with an alcohol of formula (HO—X); their corresponding alcohols can be effectively removed from the reaction composition according to the reaction conditions described below, which routinely leads to a particularly good yield and also simplifies the requirements for the reaction design.

Particularly preferred is a method of manufacture according to the invention of a composition according to the invention, wherein the conversion of the cannabidiolic acid ester of formula (IX) with the alcohol of formula (HO—X) takes place at a pressure that is lower than 1013 hPa, preferably at a pressure in the range of 5 to 500 hPa.

It is particularly advantageous not to carry out the reaction at standard pressure, but under vacuum, since this enables an efficient removal of the developing alcohol of formula HO—Y (e.g. methanol, ethanol, n-propanol, iso-propanol, n-butanol, sec-butanol, iso-butanol, tert-butanol) from the reaction composition and therefore promotes the progress of the reaction. The alcohol of formula HO—Y, which is generated through transesterification, is preferably removed from the reaction composition using distillation.

Particularly preferred is a method of manufacture according to the invention of a composition according to the invention including the following step for the manufacture of the cannabidiolic acid ester of formula (IX):

Conversion of menthadienol with an olivetolic acid ester to yield the corresponding cannabidiolic acid ester of formula (IX) in a continuous process.

It was surprisingly discovered, in particular, that the conversion of menthadienol with an olivetolic acid ester to yield the corresponding cannabidiolic acid ester of formula (IX) proceeds at a very high reaction speed, so that the process can be carried out in a continuous procedural method with high space-time yield. In the course of the corresponding study, a solution of the two precursors together with a solution of a Lewis acid catalyst was pumped continuously into a stirred reaction chamber and subsequently it was introduced into a saturated aqueous sodium bicarbonate solution in order to hydrolyze the catalyst and to prevent further reactions to byproducts.

The conversion of menthadienol with an olivetolic acid ester can be carried out in different solvents, such as e.g. methylene dichloride, chlorobenzene, toluene, xylene and cyclohexane, whereby methylene dichloride and chlorobenzene display much higher yields, however, for trade and hygiene reasons high-boiling chlorobenzene is to be favored.

As catalysts (Lewis) acids such as boron trifluoride*etherate, boron trifluoride*acetic acid, titanium tetrachloride, p-toluenesulfonic acid or methanesulfonic acid are suitable, whereby boron trifluoride*etherate achieves particularly good results.

The invention also relates to a method for the manufacture of delta-9-tetrahydrocannabinol, comprising the manufacture of a composition according to the invention, wherein the composition according to the invention is preferably manufactured by means of a method according to the invention (as defined above).

It is particularly advantageous to synthesize delta-9-tetrahydrocannabinol based on a composition according to the invention (whereby this composition is preferably manufactured by means of a method according to the invention (as defined above)), since the composition according to the invention that is produced intermediately as well as compound cannabidiol (X), which is usually subsequently, intermediately generated, display themselves individual biological activities, and therefore can be isolated from the process to a certain extent in order to be used as cannabinoid active agents themselves. Furthermore, discontinuation of the process, storage of the compositions according to the invention that are produced intermediately and continuation of the synthesis at a later stage at the same or a different place are advantageously possible.

Particularly preferred is a method for the manufacture of delta-9-tetrahydrocannabinol according to the invention comprising the manufacture of a composition according to the invention comprising one or multiple compound(s) of formula (A) and/or one or multiple salt(s) thereof, preferably one or multiple pharmaceutically acceptable salt(s) of a compound of formula (A),

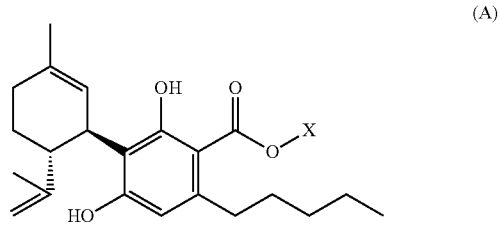

(A)

wherein X is an aliphatic residue without or with one, two, three or more than three hydroxyl groups, wherein the total number of C-atoms in the aliphatic residue X is not greater than 15, preferably not greater than 12, and wherein the aliphatic residue is
saturated or unsaturated
and
branched or unbranched
and
acyclic or cyclic, wherein the molar ratio of the total amount of compounds of formula (A) and salts thereof, preferably pharmaceutically acceptable salts, to the amount of cannabidiol (if present) in the composition is greater than 1:1, preferably greater than 5:1, particularly preferably greater than 10:1
and simultaneously
the molar ratio of the total amount of compounds of formula (A) and salts thereof, preferably pharmaceutically acceptable salts, to the amount of compounds of formula (I) (if present)

(I)

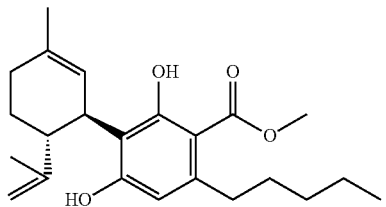

is greater than 1:1, preferably greater than 5:1, particularly preferably greater than 10:1,
wherein the composition according to the invention is manufactured according to a method according to the invention including the following step:
Conversion of a cannabidiolic acid ester of formula (IX)

(IX)

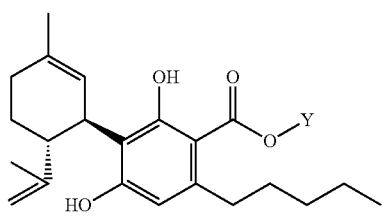

wherein Y is an organic residue,
with an alcohol of formula HO—X,
wherein
X has the meaning specified above and
wherein Y is different from X and selected in such a way that the alcohol of formula HO—Y that is generated during the conversion boils at a lower temperature at 1013 hPa than the used alcohol of formula HO—X.
Particularly preferred is a method for the manufacture of delta-9-tetrahydrocannabinol according to the invention, wherein the manufactured composition according to the invention is treated in a way that the compound of formula (A) that is contained in the composition, is saponified and decarboxylated to generate compound (X) (cannabidiol).

(X)

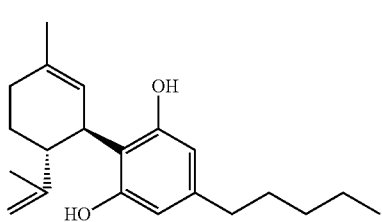

Particularly preferred is a method for the manufacture of delta-9-tetrahydrocannabinol according to the invention, wherein compound (X), which is present after the decarboxylating saponification, is cyclized to yield delta-9-tetrahydrocannabinol, preferably in the absence of halogenated solvents.

(X)

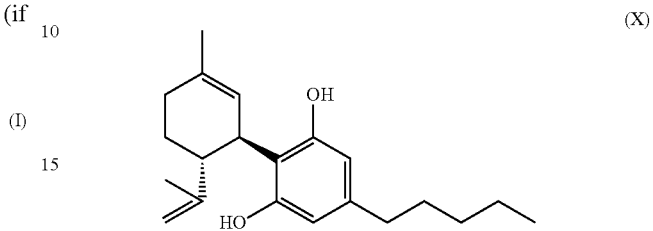

Surprisingly, chlorinated methylene chloride, which is used in cyclizations in the prior art, could be replaced in our own studies by nonhazardous methyl tert-butyl ester without causing any disadvantages. This also worked using concentrations of up to 20 wt.-% cannabidiol in the starting composition.

The present invention will be explained in more detail on the basis of the examples below.

A. STUDIES ON THE EFFECT OF COMPOUNDS ACCORDING TO THE INVENTION ON CANNABINOID RECEPTORS

Binding Affinity:

In particular, the following substances III-V and XI-XIII of the generic formula (A) were examined in own studies regarding their effect on cannabinoid receptors.

III

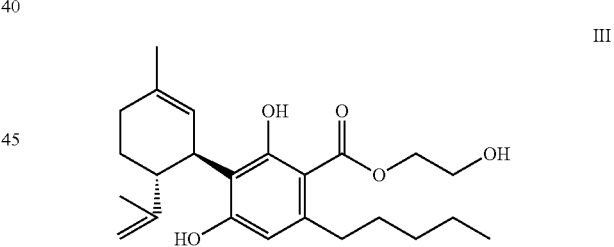

IV

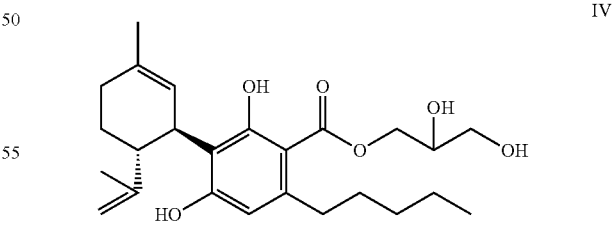

V

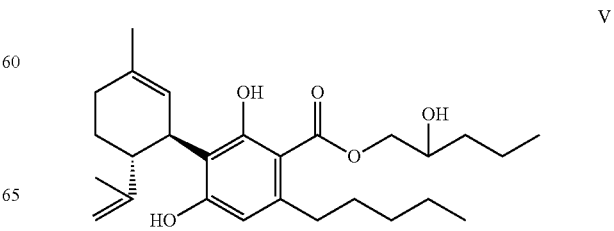

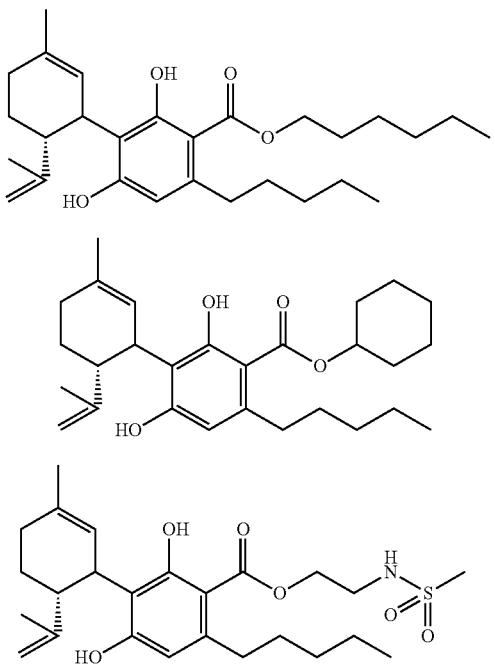

Substances III-V and XI-XIII were tested in competition studies regarding their binding affinity and their resulting binding profile for CB1 and CB2 receptors. Such studies enable the comparison of the affinity of each of the substances III-V and XI-XIII ($K_i$ values) with the affinity of another ligand for the cannabinoid receptors. The competition studies were carried out in cell membranes, which were transfected with CB1 and CB2 receptors.

To this end, membranes of human cells were used, in which the CB1 and CB2 receptors (RBHCB1M400UA and RBXCB2M400UA) with a $B_{max}$ and $K_d$ value for CP55940 for CB1 or CB2 of, for example, 1.9 pmol/mg membrane protein and 0.18 nM for CB1 and 5.2 pmol/mg membrane protein and 0.18 nM for CB2 were transfected.

In an exemplary experiment the protein concentration of the CB1 receptor-carrying membrane was 8.0 mg/mL and the one of the CB2 receptor-carrying membrane was 4.0 mg/mL. These and further values resulted from the specifications of the manufacturer of the membranes and can be easily followed by a knowledgeable person skilled in the art just as well as the techniques with which the studies were carried out. The membrane suspensions were diluted in a dilution of 1:20 with buffer solution (50 nM TrisCl, 5 nM $MgCl_2 \times H_2O$, 2.5 nM EDTA, 0.5 mg/mL BSA and pH 7.4 for CB1 binding buffer; 50 nM TrisCl, 5 nM $MgCl_2 \times H_2O$, 2.5 nM EGTA, 1 mg/mL BSA and pH 7.5 for CB2 binding buffer). [$^3$H]-CP55940 (144 Ci/mmol) was used as radioligand. In this context, exemplary concentrations were 0.10 nM with a volume of 200 µL for CB1 binding studies and 0.15 nM with a final volume of 600 µL for CB2 binding studies. The membranes were resuspended in the buffer, incubated with the radioligand and with each substance for 90 min at 30° C. Nonspecific binding was determined with the aid of the classic ligand WIN55,212-2 and 100% binding of the radioligand was determined by incubating the membrane without any other substance. After filtration of the respective preparation, it was washed nine times with the respective binding buffer and subsequently dried. The radioactivity was determined with a suitable scintillation counter. Corresponding models are already known from the literature (Granja, A. G. et al. *J. Neuroimmune Pharmacol.* 2012, 7, 1002-1016; Cumella, J. et al. *Chem Med Chem.* 2012, 7, 452-463; Di Marzo, V. et al. 2000, *J. Neurochem.*, 2000, 74, 1627-1635).

An assessment of the components was carried out in two phases. The first phase consisted of a screening with a single high dose of each substance regarding their binding abilities. The following table shows the percentage values for the binding to CB1 and CB2:

TABLE 1

Percentage binding of selected cannabinoids at cannabinoid receptors

| Substance | CB1 (% binding) | CB2 (% binding) |
|---|---|---|
| III | 77.3 ± 6.5 | 90.3 ± 2.4 |
| IV | 90.2 ± 3.8 | 101.6 ± 0.5 |
| V | 82.0 ± 8.0 | 83.9 ± 5.6 |
| XI | 92.2 ± 1.7 | 97.2 ± 3.4 |
| XII | 81.5 ± 6.8 | 99.2 ± 2.3 |
| XIII | 98.9 ± 7.8 | 104.9 ± 4.8 |

Note: The measured values 101.6±0.5 and 104.9±4.8 are based on a usual, scientifically accepted measuring inaccuracy of the used model.

Substances that display over 50% binding and therefore display displacement of [$^3$H]-CP55940, were tested in a second phase for their competition for CB1 and CB2 by incubating different concentrations of the substances together with [$^3$H]-CP55940 inside the receptor model. The resulting data was evaluated with the aid of a suitable statistics software (e.g. GraphPrism® Version 5.01). The following table shows the dissociation constants ($K_i$) for the substances as mean value+/−standard error (SEM):

TABLE 2

Dissociation constants of the cannabinoid compounds III-V and XI-XIII

| Substance | $K_i$ for CB1 (nM) | $K_i$ for CB2 (nM) | $K_i$ (CB1): $K_i$ (CB2) Selectivity for CB2 in comparison to CB1 (rounded) |
|---|---|---|---|
| III | 3,923 ± 1,547 | 374.5 ± 47.7 | 10.4 |
| IV | 2,174 ± 1,149 | 277.1 ± 78.7 | 7.8 |
| V | 538.2 ± 53.9 | 66.7 ± 13.1 | 8.1 |
| XI | 538.2 ± 53.9 | 510 ± 29 | 1 |
| XII | 538.2 ± 53.9 | 67 ± 4 | 37 |
| XIII | 538.2 ± 53.9 | 0.012 ± 0.001 | 22.5 |

In comparison, substance WIN55,212-2, which was used as classical nonspecific ligand as positive control for such an experiment, showed a dissociation constant of 28.8+/−1 nM for CB1 and 3.7+/−1 nM for CB2 and therefore corresponds to the literature values (e.g. Pertwee, R. G. et al. *Pharmacol. Rev.* 2010, 62, 588-631).

Conclusion/Comparative Evaluation:

The cannabinoid substances III-V and XI-XIII bind to cannabinoid receptors in nM concentrations and therefore at physiological doses. They are weak ligands for CB1 receptors and bind preferentially to CB2 receptors. Their selectivity for CB2 receptors particularly predestines them for the use as CB2 receptor modulators (as described above).

Cannabinoids known in the literature and substances that do not number among the classical cannabinoids, are divided into groups on the basis of their affinity for CB1 and CB2 receptors (Pertwee, R. G. et al. *Pharmacol. Rev.* 2010, 62, 588-631). The group assignment and hence the pharmacodynamic mechanism determines the mode of the effect of the substances.

While CBD exerts a very weak effect with low affinities (CB1: 4,350 to >10,000 nM; CB2: 2,399 to >10,000 nM), delta-9-THC is a strong ligand for both receptors with CB1: 5.05 to 80.3 nM and CB2: 3.13 to 75.3 nM, which also explains its strong effects on the central nervous system (also side effects) and simultaneous peripheral effects (and side effects). The psychotropic effects of delta-9-THC are attributed to its complex interaction with the CB1 receptor. The activation of the CB1 receptor causes undesired effects on the psyche (and the circulation), on the contrary the activation of the CB2 receptor does not seem to do this, which also is because of the localization of the CB2 receptors in the periphery (Atwood, B. K. Prog. Neuropsychopharmacol. Biol. Psychiatry 2012, 38, 16-20).

The cannabinoids described herein display an advantageous and unique distribution of their binding affinity (see table 2). Their binding affinity towards an attenuated, but not completely abrogated activation of the CB1 receptor predestines the substances as pharmaceuticals. The evidence of an advantageous effect of CB2 modulators in pathological situations that have not been accessible to pharmacotherapy to date, has grown strongly over the past couple of years. The two most important indications for CB2 modulators are neuroinflammation and pain (Cheng, Y., Hitchcock, S. A. Expert Opin. Invest. Drugs 2007, 16, 951-965; Guindon, J., Hohmann, A. G. J. Pharmacol. 2008, 153, 319-334). Furthermore, substances according to the invention can also influence the following pathological situations via CB2 modulation: Systemic inflammation, osteoporosis, cancer, transplantation-induced pathological conditions, different pathological conditions of the central nervous system including drug addiction and anxiety states as well as liver conditions (Bab, I. et al. Ann. Med. 2009, 41, 560-567; Karsak, M. et al. Science 2007, 316, 1494-1497; Mallat, A., Lotersztajn, S. Dig. Dis. 2010, 28, 261-266; Nagarkatti, M. et al. Trends Pharmacol. Sci. 2010, 31, 345-350; Patel, K. D. et al. Curr. Med. Chem. 2010, 17, 1393-1410; Xi, Z. X. et al. Nat. Neurosci. 2011, 14, 1160-1166).

Signal Transduction at CB1 and CB2 Transfected CHO Cells:

Dermuth et al. (2006) describe the signal transduction via cannabinoid receptors. The mode of signal transduction has already been explained sufficiently.

After the binding affinity of the substances according to the invention designated above was established, their intrinsic activity was examined on the basis of a functional assay of cannabinoid receptor transfected cells. To this end, CHO cells (immortalized "Chinese Hamster Ovary" cells) were transfected with CB1 and CB2 receptors via the transfer of cDNA. The hence obtained transfected cells (CHO-CB1 and CHO-CB2) were transiently transfected with plasmid CREluc, which contains several (e.g. 6) consensus cCAMP responsive elements (CRE) and firefly luciferase (luc). The techniques necessary for this purpose are accessible to the knowledgeable person skilled in the art via the relevant technical literature.

In order to investigate the agonistic activity, the transfected cells (CHO-CB1-CREluc and CHO-CB2-CREluc) were treated either with increasing concentrations of the molecules according to the invention or with WIN55,212-2 (WIN), which is a classical nonspecific agonist for CB1 as positive control, incubated and subsequently tested for their activity through the addition of luciferin (a chemoluminescent substrate of firefly luciferase). Forskolin, an adenylate cyclase activator, was used as positive control, since its activation of the cAMP pathway takes place independently from the cannabinoid receptors. In order to investigate a possible antagonism at the CB1 receptors, the CHO-CB1-CREluc cells were pre-incubated with the test substances and then stimulated with WIN. In order to investigate the agonism at the CB2 receptors, CHO-CB2-CREluc cells were treated with either increasing concentrations of substances according to the invention or with WIN, also a classical nonspecific agonist for CB2 as positive control, for a short period of time (15 min). Then forskolin was added and the preparation was incubated. In order to confirm the agonistic effect at CB2 receptors, CHO-CB2-CREluc were furthermore incubated with the specific antagonist AM630 (Ross et al., 1999). After an adequate incubation time and subsequent lysis, the luciferase activity was measured. The background activity (buffer) was subtracted from the result, respectively. FIG. 1 (Analysis scheme of the signal transduction at CB1 and CB2 transfected CHO cells) depicts a possible analysis scheme for illustration of the activity of substances according to the invention.

Substances according to the invention possess a particularly advantageous ratio of activation of CB1 receptors to CB2 receptors. Preferably, CB2 receptors are activated by substances according to the invention, whereas CB1 receptors are only activated to a negligible extent or not at all or are even inhibited.

Glyceryl cannabidiolate shows a weak activation of CB1 receptors and a strong activation of CB2 receptors. 2-Hydroxyethyl cannabidiolate and 2-hydroxypentyl cannabidiolate show a strong activation of the CB2 receptor and inhibit the CB1 receptor. Hexyl cannabidiolate shows antagonism at both receptors, while cyclohexyl cannabidiolate has an antagonistic effect on the CB1 receptor. N-Methyl-sulfonyl cannabidiolate shows, besides a high binding affinity for CB1 and CB2, an antagonistic effect on CB1 and an agonistic effect on CB2.

TABLE 3

Agonism and antagonism of cannabinoids according to the invention at cannabinoid receptors

| Substance | CB1 | CB2 |
|---|---|---|
| 2-Hxdroxyethyl cannabidiolate (compound III) | − | + |
| Glyceryl cannabidiolate (compound V) | + | + |
| 2-Hydroxypentyl cannabidiolate (compound IV) | − | + |
| Hexyl cannabidiolate (compound XI) | + | + |
| Cyclohexyl cannabidiolate (compound XII) | − | 0 |
| N-Methyl-sulfonyl cannabidiolate (compound XIII) | − | + |

Legend:
−: Antagonism
+: Agonism
0: no activity

Endogenous Signal Transduction in Jurkat Cells:

CB2 receptor agonists are particularly suitable for triggering immunomodulating effects. There is evidence for the inhibition of T cell activation by CB2 agonists. Particularly in Jurkat T cells CB2 agonists inhibit their activation according to Börner et al. (2009). Transferred to the physiological situation such functionality can be beneficial to the prophylaxis and therapy of immune diseases, e.g. autoimmune diseases such as multiple sclerosis.

Substances according to the invention were investigated in an accepted Jurkat T cell model. The underlying mechanism is based on the fact that the transcriptional activity of lymphokines, such as e.g. the one of IL-2, is based on the coordinated activation of different transcription factors, such as e.g. NFAT and NF-κB. The effect of the substances according to the invention on said factors was evaluated in-vitro with the aid of a luciferase-coupled construct (KBF-luc). Thereby, an activation of transiently transfected cells (Jurkat T cells) through PMA (plus ionomycin in case of NFAT activation), driven by a NF-κB or NFAT dependent promoter, leads to a strong induction of luciferase gene expression. The inhibition of the luciferase activity was measured as a function of the dose rate of the substance according to the invention. A knowledgeable person skilled in the art can easily follow such procedure from the literature (e.g. in Yuan et al. (2002), Sancho et al. (2003), Do et al. (2004) and Cencioni et al. (2010)).

A characteristic of substances according to the invention may be the inhibition of the NF-κB or NFAT dependent activation of the T cells. Thus, for substance N-methylsulfonyl cannabidiolate according to the invention a strong inhibition of the activation of T cells via NF-κB and NFAT is detectable. The substances 2-hydroxyethyl cannabidiolate, glyceryl cannabidiolate and 2-hydroxypentyl cannabidiolate according to the invention show an inhibition of the NFAT dependent activation of T cells.

B. SYNTHESIS OF DELTA-9-THC VIA 2-HYDROXYETHYL CANNABIDIOLATE (III)

Step 1: Coupling Step (in the Continuous Process); Synthesis of Cannabidiolic Acid Methyl Ester (I)

300 g (2.0 mole) menthadienol and 476 g (2.0 mole) olivetolic acid ester are dissolved at ca. 22° C. in 1,370 g of chlorobenzene (2,000 mL solution A), likewise 94 g (0.66 mole) boron trifluoride*etherate are dissolved in 640 g of chlorobenzene at ca. 22° C. (666 mL solution B)., Solution A at a flow rate of 72 mL/min and solution B at a flow rate of 24 mL/min are pumped into a stirred reaction chamber via two separate dosing pumps, from the reaction chamber the reaction composition runs via a PTFE hose into a stirred solution of 1,000 g of sodium bicarbonate. The total reaction time is ca. 20 min. After termination of the metering the hydrolyzed reaction solution is stirred for a further 30 min.

Then the hydrolyzed reaction solution is transferred into a 5 L jacket reaction vessel, the aqueous phase is separated and the solvent chlorobenzene is removed in vacuo. Ca. 2,000 g of toluene are added to the remaining 730 g of raw material and the unreacted olivetolic acid ester is extracted through the addition of 1,200 g 1% aqueous sodium hydroxide solution (four times). After acidifying with semi conc. sulfuric acid and re-extraction of this aqueous phase, ca. 30% (140 g) of non converted olivetolic acid ester are recovered.

There are ca. 520 g of cannabidiolic acid methyl ester (I) in the toluene phase, which corresponds to a theoretical yield of ca. 70%. This first intermediate serves as starting material for the following transesterification.

Step 2: Transesterification, Synthesis of 2-Hydroxyethyl Cannabidiolate (III):

The toluene is removed by destillation and to the remaining first intermediate 600 g of ethylene glycol are added under stirring followed by a solution of 85 g of potassium hydroxide in 300 g ethylene glycol. A vacuum of ca. 0.5 bar is applied and it is heated to 120° C. for 2 h, whereby ca. 40 g of methanol distill off. The resulting product composition mainly comprises 2-hydroxyethyl cannabidiolate (III).

Step 3: Saponification/Decarboxylation, Synthesis of Cannabidiol (X):

Subsequently, the temperature is increased to 150° C. and it is stirred at this temperature for 2 h. The product composition resulting from the transesterification comprising mainly 2-hydroxyethyl cannabidiolate (III) is cooled down to ca. 40° C. and 500 g of water as well as 500 g of n-heptane are added and ca. 150 g of semi conc. sulfuric acid are added for neutralization. After phase separation, the solvent is removed using a rotary evaporator and the remainder is distilled over a thin-film evaporator using a vacuum of ca. 0.5 mbar and a jacket temperature of 230° C. 310 g of cannabidiol (X) are obtained in the form of a viscous, yellowish oil with a purity of 85%, which corresponds to a theoretical yield of 60% in relation to the used cannabidiolic acid ester.

This viscous, yellowish oil is then recrystallized in ca. 200 g of n-heptane at ca. −5° C., after which 210 g of white crystallizate with a purity of 99% cannabidiol (X) are obtained.

Step 4: Cyclization, Synthesis of Delta-9-THC:

50 g of pure cannabidiol are dissolved in 250 g methyl-tert-butylether and 40 g of boron trifluoride*acetic acid complex are added under stirring within 10 min at ca. 22° C. It is stirred for 3 h at said temperature and then 200 g of ice water are added, the organic phase is washed with sodium bicarbonate solution and the solvent is removed using a rotary evaporator. The remaining raw material of ca. 50 g contains 74% Δ-9-tetrahydrocannabinol (delta-9-THC), 25% of side products as well as <1% cannabidiol. After purification by column chromatography, 30 g of pure delta-9-THC are obtained, which corresponds to a theoretical yield of 60%.

The steps of the synthesis of delta-9-THC via 2-hydroxyethyl cannabidiolate (III) are depicted schematically below:
Step 1: Coupling Step (in the Continuous Process); Synthesis of Cannabidiolic Acid Methyl Ester (I)

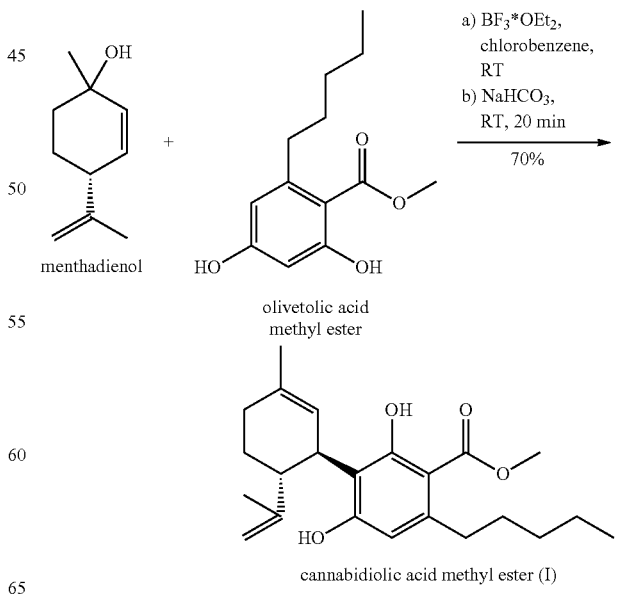

Step 2: Transesterification, Synthesis of 2-Hydroxyethyl Cannabidiolate (III):

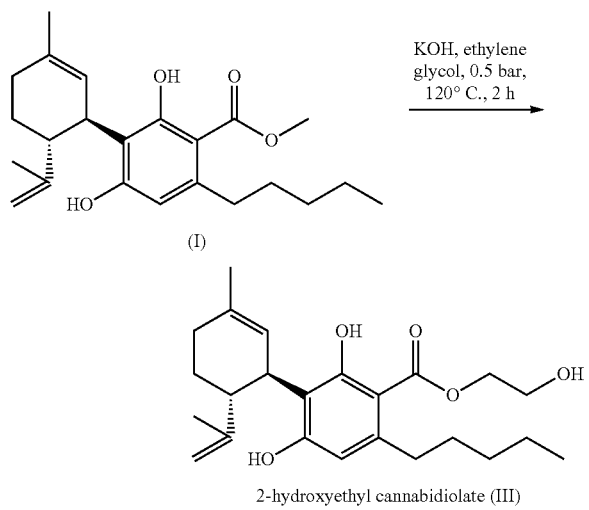

Step 3: Saponification/Decarboxylation, Synthesis of Cannabidiol (X):

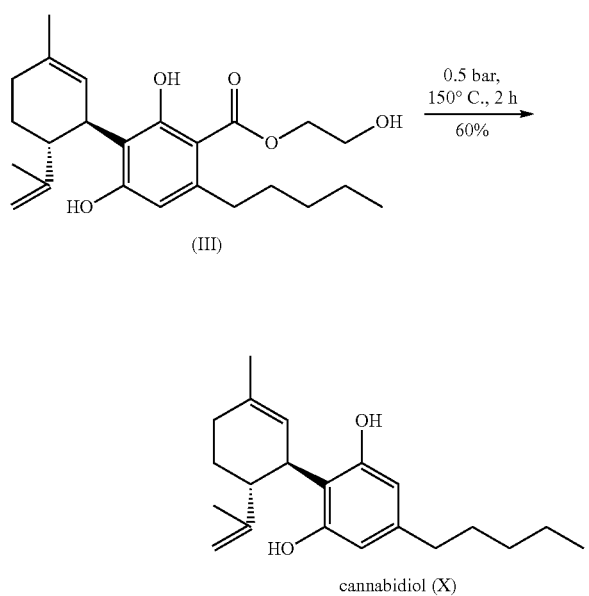

Step 4: Cyclization, Synthesis of Delta-9-THC:

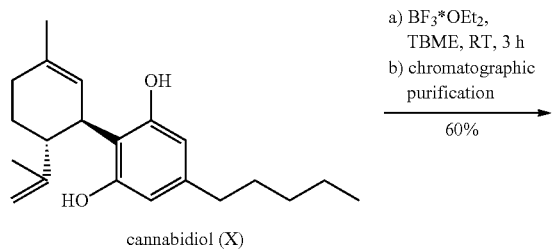

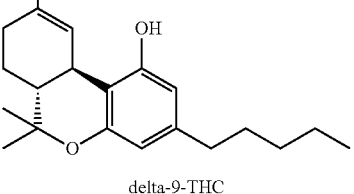

delta-9-THC

C. APPLICATION EXAMPLES

The use of compounds of formula (A) according to the invention is explained in greater detail by means of the following examples of preferred pharmaceutical formulations according to the invention. The use of compound (V) is preferred in this respect.

Application Example 1—Capsules According to the "Neuen Rezeptur Formularium", 18$^{th}$ Addition, 2001

Preparation for 1 Capsule

|  | 2.5 mg | 5 mg | 10 mg |
| --- | --- | --- | --- |
| Compound of formula (A) | 0.0025 g | 0.005 g | 0.010 g |
| Hydrogenated fat (slip point: 37-40° C.; OH-number: 7-17; sap-number: 245-260) | to 0.430 g | to 0.430 g | to 0.430 g |
| Two-piece hard gelatin capsule shell, size 1 | 1 piece | 1 piece | 1 piece |

Preparation for 30 Capsules Including 10% Excess of the Melt

|  | 2.5 mg | 5 mg | 10 mg |
| --- | --- | --- | --- |
| Compound of formula (A) | 0.083 g | 0.165 g | 0.33 g |
| Hydrogenated fat (slip point: 37-40° C.; OH-number: 7-17; sap-number: 245-260) | to 14.2 g | to 14.2 g | to 14.2 g |
| Two-piece hard gelatin capsule shell, size 1 | 30 pieces | 30 pieces | 30 pieces |

Preparation for 60 Capsules Including 5% Excess of the Melt

|  | 2.5 mg | 5 mg | 10 mg |
| --- | --- | --- | --- |
| Compound of formula (A) | 0.158 g | 0.315 g | 0.63 g |
| Hydrogenated fat (slip point: 37-40° C.; OH-number: 7-17; sap-number: 245-260) | to 27.1 g | to 27.1 g | to 27.1 g |
| Two-piece hard gelatin capsule shell, size 1 | 60 pieces | 60 pieces | 60 pieces |

1. In a horizontally adjusted capsule filling machine the inserted two-piece hard gelatin capsule shells are opened, the fixed lower parts of the capsules are exposed and made available for filling.
2. A little bit more hydrogenated fat than required for the preparation is melted in a beaker. In-process testing: The hydrogenated fat melting must be clear at visual inspection. It may be of a faintly yellow color.

3. In a second beaker molten hydrogenated fat is added to the compound of formula (A) according to the preparation amount specified above. The substance is dissolved under stirring with a glass rod. In-process testing: The fat melting must be clear at visual inspection. It may be of a faintly yellow color.
4. The fat melting is left inside the still warm, but no longer boiling water bath until the last capsule is filled, or it is removed from the water bath and reheated as needed. In-process testing (to be repeated from time to time): The temperature of the melting has to be between 35 and 45° C.
5. Ca. 1 mL of the fat melting is drawn up into a 1 mL disposable syringe preferably via a wide-lumen hollow needle (see under "Pharmazeutische Erläuterungen—Herstellungstechnik und Abfüllung"). Two capsule lower parts are filled immediately. In-process testing: The upper rim of the lower part of the capsule has to be fully coated with fat melting from the inside. The surface of the liquid has to be planar or slightly concave.
6. The syringe is refilled and the filling of further capsules is continued until all of the capsules are filled. The empty space, which is generated in the capsule through the cooling of the melting may not be refilled. In-process testing: Only a small residue of fat melting of about 1 mL is supposed to remain in the beaker.
7. After solidification of the fat melting in the lower parts of the capsules, the capsules are closed tightly.

In-process testing: The surface of the fat melting has to have the same opaque appearance in all of the capsule lower parts.

End-product testing: The closed capsules have to have a uniform appearance. Only as needed: The single mass of all capsules has to be between 460 and 540 mg each.

Application Example 2—Oily Solutions According to the "Neuen Rezeptur Formularium", 19<sup>th</sup> Addition, 2002

Ingredients

|  | 20 g | 100 parts by weight |
| --- | --- | --- |
| Compound of formula (A) (see „Bezugsquellennachweis für Rezepturbestandteile", chapter III.2.) | 0.5 g | 2.5 parts |
| Medium-chain triglycerides | to 20.0 g | to 100.0 parts |

1. The compound of formula (A) is liquefied inside the storage vessel through gentle heating.
2. The compound of formula (A) is weighed into a beaker and dissolved in the medium-chain triglycerides under heating and stirring.

End-product testing: The solution must be clear at visual inspection. It may be of a faintly yellow color.

The invention claimed is:
1. A compound selected from the group consisting of:

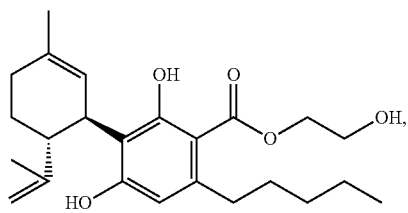

III

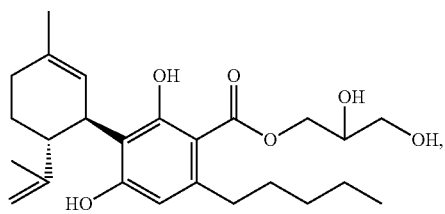

IV

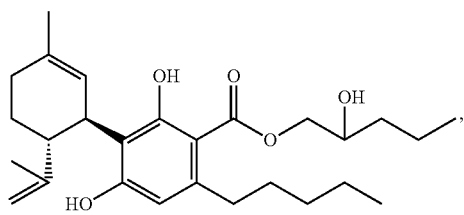

V

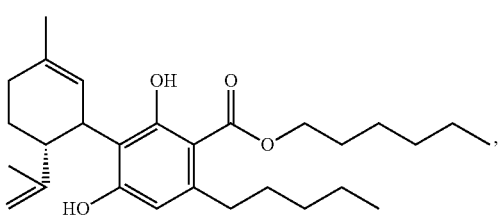

XI

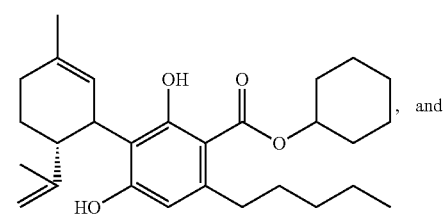

XII

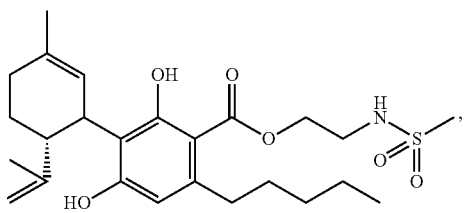

XIII or a salt thereof.

2. A composition comprising one or more compounds and/or salts of claim 1.

3. A pharmaceutical composition comprising one or more compounds and/or salts of claim 1.

4. A method for manufacturing a compound of claim 1 comprising converting menthadienol with an olivetolic acid ester to derive the compound.

5. A method for manufacturing cannabidiol comprising:
   (a) obtaining a compound or salt of claim 1; and
   (b) subjecting the compound or salt to saponification and decarboxylation to generate cannabidiol.

6. A composition comprising:
   (a) one or more compounds selected from the group consisting of:

or a salt thereof;

(b) optionally, cannabidiol, wherein if cannabidiol is present, the ratio of the total amount of the one or more compounds of (a) and/or salts thereof to the total amount of cannabidiol is greater than 1:1; and (c) optionally, a compound of Formula (I)

wherein if a compound of Formula (I) is present, the ratio of the total amount of the one or more compounds of (a) and/or salts thereof to the total amount of the compound of Formula (I) is greater than 1:1.

7. A medicine comprising a composition of claim 6.

8. A method for the therapeutic treatment of a human or animal comprising administering a composition of claim 6 to the human or animal, wherein the therapeutic treatment provides:
- an appetite-stimulating effect,
- an anti-emetic effect to inhibit nausea and vomiting,
- reduction of muscular cramps and spasticity,
- alleviation of pain symptoms,
- alleviation of migraine symptoms,
- reduction of intraocular pressure related to glaucoma,
- mood enhancement,
- immunostimulation, and/or
- antiepileptic effect.

9. A method for manufacturing a composition of claim 6 comprising converting menthadienol with one or more olivetolic acid esters to derive the one or more compounds and/or salts of (a) in the composition.

10. A method for manufacturing cannabidiol comprising:

(a) preparing a composition of claim 6; and (b) subjecting the one or more compounds of (a) and/or salts in the composition to saponification and decarboxylation to generate cannabidiol.

\* \* \* \* \*